(12) United States Patent
Rolland

(10) Patent No.: US 9,643,825 B2
(45) Date of Patent: May 9, 2017

(54) OPTICAL SYSTEM FOR DETECTING THE STATE OF WINDING OF A CABLE ON A WINCH

(75) Inventor: Yves Rolland, Locmaria-Plouzane (FR)

(73) Assignee: THALES, Courbevoie (FR)

( * ) Notice: Subject to any disclaimer, the term of this patent is extended or adjusted under 35 U.S.C. 154(b) by 351 days.

(21) Appl. No.: 14/241,351

(22) PCT Filed: Aug. 14, 2012

(86) PCT No.: PCT/EP2012/065882
§ 371 (c)(1),
(2), (4) Date: Apr. 14, 2014

(87) PCT Pub. No.: WO2013/029990
PCT Pub. Date: Mar. 7, 2013

(65) Prior Publication Data
US 2014/0239165 A1    Aug. 28, 2014

(30) Foreign Application Priority Data
Sep. 2, 2011   (FR) ...................................... 11 02671

(51) Int. Cl.
*B66D 1/56* (2006.01)
*G02B 6/35* (2006.01)
(Continued)

(52) U.S. Cl.
CPC .................. *B66D 1/56* (2013.01); *B66D 1/28* (2013.01); *G01N 21/25* (2013.01); *G02B 6/35* (2013.01)

(58) Field of Classification Search
CPC . B66D 1/28; B66D 1/56; B66D 1/485; B66D 1/54; B65H 2511/20;
(Continued)

(56) References Cited

U.S. PATENT DOCUMENTS

| 4,749,872 A * | 6/1988 | Asada ................... H04N 1/0473 250/252.1 |
| 4,931,637 A * | 6/1990 | Succari ................ H04N 1/0281 250/227.26 |
| 5,642,553 A * | 7/1997 | Leifeld ................... D01G 15/24 19/112 |
| 2005/0219526 A1* | 10/2005 | Peng .................... G01N 21/532 356/338 |

(Continued)

FOREIGN PATENT DOCUMENTS

| CN | 101575074 A | 11/2009 |
| GB | 2295453 A1 | 5/1996 |

(Continued)

*Primary Examiner* — Thanh Luu
*Assistant Examiner* — Jennifer Bennett
(74) *Attorney, Agent, or Firm* — Baker & Hostetler LLP

(57) ABSTRACT

A system allowing automatic detection of the end of winding of a cable on a winch comprises an optical detector which emits, in the direction of the cable, a light beam which illuminates a given zone through which the cable travels in the course of its winding. The detector is associated with a specific marking, strongly reflecting, positioned on a section of the cable close to its end, such that, when this section enters into the zone illuminated by the detector, it reflects the beam in the direction of the detector which detects this reflected beam and which then signals that the cable is almost at the end of winding. The detector, placed in a fixed position at a given distance from the cable, is also associated with a light waveguide interposed between the cable and the optical detector.

5 Claims, 4 Drawing Sheets

(51) Int. Cl.
  *G01N 21/25* (2006.01)
  *B66D 1/28* (2006.01)
(58) Field of Classification Search
  CPC ............ B65H 2511/40; B65H 2511/50; B65H 2511/51; B65H 2511/512; B65H 2511/411; B65H 2553/40; B65H 2553/414; B65H 2553/41; B65H 2553/44; G01N 21/25; G01N 21/55; G01N 21/952; G02B 6/35; G02B 6/3514
  USPC ......... 250/227.11, 221, 216, 559.01, 559.29, 250/559.3, 559.4, 559.44, 239
  See application file for complete search history.

(56) References Cited

U.S. PATENT DOCUMENTS

2008/0035324 A1* 2/2008 Ciglenec ................ E21B 19/02
                                                    166/64

FOREIGN PATENT DOCUMENTS

| JP | 5-248821 A | 9/1993 |
| JP | 6-47851 U | 6/1994 |
| JP | 7-98384 A | 4/1995 |
| JP | H10-203787 A | 8/1998 |
| JP | 2000-026075 A | 1/2000 |
| JP | 2000-26075 A | 1/2000 |
| JP | 2000-250603 A | 9/2000 |
| JP | 2005077764 A * | 3/2005 |
| WO | 2010014048 A1 | 2/2010 |

* cited by examiner

Fig. 2    (Cross-section A-A)

Fig. 3 (Cross-section A-A)

OPTICAL SYSTEM FOR DETECTING THE STATE OF WINDING OF A CABLE ON A WINCH

CROSS-REFERENCE TO RELATED APPLICATIONS

This application is a National Stage of International patent application PCT/EP2012/065882, filed on Aug. 14, 2012, which claims priority to foreign French patent application No. FR 1102671, filed on Sep. 2, 2011, the disclosures of which are incorporated by reference in their entirety.

FIELD OF THE INVENTION

The invention relates to the field of automatic systems for deploying and recovering objects by means of a winch or any similar device that can be used to unwind and wind a cable, at the end of which is attached the object to be deployed. It relates more particularly to the field of airborne winches, installed on a helicopter for example, for automatically placing and recovering miscellaneous objects in and from water, such as a recovery pod or a dipped sonar.

BACKGROUND

When there is a desire to use a winch, however, automatically, a critical operation in its use consists in determining the moment when, the cable being almost fully rewound, the winch has to be stopped.

In practice, if the winding is stopped too late, the object linked to its end can strike the platform supporting the winch and thereby even damage this structure and injure the operator working on this platform and even be itself damaged. Conversely, if this winding is stopped too early, the object is situated too far from the platform to be able to be recovered in total safety, without the risk of bodily injury or equipment damage.

Consequently, a visual reference mark is usually placed on the cable which makes it possible to visually determine the moment when the cable can be considered to be sufficiently wound on the winch. The visual reference mark consists, very generally, simply and effectively, of a white colored reference mark, such as an annular marking painted directly on the cable.

Thus, in the case of manual use of the winch, it is the operator situated on the platform who, when rewinding the cable, on seeing the white colored reference mark appear in his or her field of vision, determines the appropriate moment to order the slowing down and the stopping of the winch.

Similarly, in the case of partially or totally automated use, an optical sensor is used, charged with monitoring the travel of the cable and capable of detecting the appearance, within its observation sector, situated in proximity to the platform, of the portion of white colored cable. When the optical device detects the passing of this reference mark, it sends an indication to the means controlling the winch motor informing them that the winch has to be stopped within a short delay.

The use of an optical detection system to detect the appearance of the end-of-winding reference mark offers numerous advantages, among which can be cited the ease of use. In practice, this only requires the positioning, in proximity to the cable, on a mechanical structure linked to the platform, of an optical sensor whose beam is directed toward the cable. However, in the case of an airborne winch system mounted on a platform, installed in the interior of an aircraft for example, and intended to place a given object in water and keep it immersed for a given time, then to rapidly raise the object back onboard the aircraft, the use of an end-of-winding optical detection system, placed at a given distance from the cable and securely attached to the platform, poses at least two difficulties.

The first difficulty consists in producing, without any doubt, the detection by the optical sensor of the white colored reference mark, within a restricted observation zone, while the cable is traveling at a significant speed, possibly reaching 10 m/s for example. In practice, the detection is generally made by means of an optical sensor, configured to emit a narrow light beam and detect the reflection of the light beam by a reflecting object. Consequently, the detection is all the more definite when the detector is closer to the detected object and the object concerned reflects a greater portion of the light beam. Now, as illustrated in FIG. 1, with regard to a cable, with a substantially circular section, only a small portion of the surface of the cable is likely to reflect the light beam in the direction of the sensor. The reflected energy is therefore weak. Consequently, the sensor may detect nothing even in the presence of the portion of cable bearing the white colored reference mark, which is intrinsically more reflecting than the rest of the uncolored metal cable which has a matt appearance.

The second difficulty is linked to the fact that, because of its rapid rise, the cable brings up with it water which is splashed into the space situated between the detector and the cable, in the detection zone. This splashing of water on the one hand causes the efficiency of the detector to be reduced and on the other hand provokes spurious reflections inasmuch as, independently of the presence of the colored reference mark in the detection zone, the water droplets scattered in the detection zone can reflect the beam emitted by the detector with a sufficient intensity to provoke an incorrect detection of the end of the rewinding operation.

SUMMARY OF THE INVENTION

Thus, the problem which is posed consists, with an optical detector, in detecting, definitely and with a minimum of false detections, the passage of a white mark on a matt and rather dark cable moving at high speed, the detection zone being situated in an optically disturbed ambience. Consequently, one aim of the invention is to propose a simple solution that makes it possible to resolve this problem.

To this end, the subject of the invention is a system for monitoring the travel of a cable wound on a winch, of the type comprising an active optical detection device placed upstream of the winding zone of the cable, at a given distance D therefrom, and means for forming, on a section of the cable, a strongly reflecting colored zone, securely attached to the cable, the active optical detection device comprising a light source emitting a light beam in the direction of the cable, the light beam illuminating the section of the cable situated in the zone of illumination at the instant concerned, and means for receiving the light rays reflected by the surface of the cable illuminated by the light beam, the means for forming a colored reference mark being positioned on the cable in such a way that, when the colored reference mark is placed in the light beam emitted by the sensor, the light beam reflected by the cable exhibits a sufficient intensity to be detected. According to the invention, the system also comprises a light waveguide interposed between the optical detection device and the cable. Advantageously, the waveguide has a free end directed toward the cable. Advantageously, the waveguide has a fixed end securely attached to the light source. Advantageously, the length of the guide is defined in such a way that the distance between the free end of the guide and the cable is minimized.

According to a particular embodiment, the free end of the light waveguide has a non-planar surface.

According to another particular embodiment, the free end of the light waveguide has a concave surface concentric with the surface of the cable.

According to a preferred form of the preceding embodiment, the length of the light waveguide is defined in such a way that the water driven by the cable in its movement forms, between the end of the guide and the surface of the cable, a film of water which fills the space between the end of the guide and the surface of the cable and thus enhances the guiding of the light beam reflected by the surface of the cable toward the detection device.

According to another particular embodiment, the optical waveguide has lateral faces covered with a thin layer of reflecting material.

BRIEF DESCRIPTION OF THE DRAWINGS

The features and advantages of the invention will be better understood from the following description, a description which is based on the appended drawings which show.

DETAILED DESCRIPTION

The description which follows presents the system according to the invention in a particular application. This particular case of use, the object of which is to highlight the advantages of the invention, obviously in no way limits the scope of it to this single use, the scope of the invention extending notably to any application for which a contactless detection of a marking placed on a traveling object facing an optical detector must be produced.

The particular case of use described relates to the detection of the complete winding of the cable of a winch installed on a platform mounted on a helicopter, this winch being, for example, intended to be a detection system of sonar type.

Figure 1:
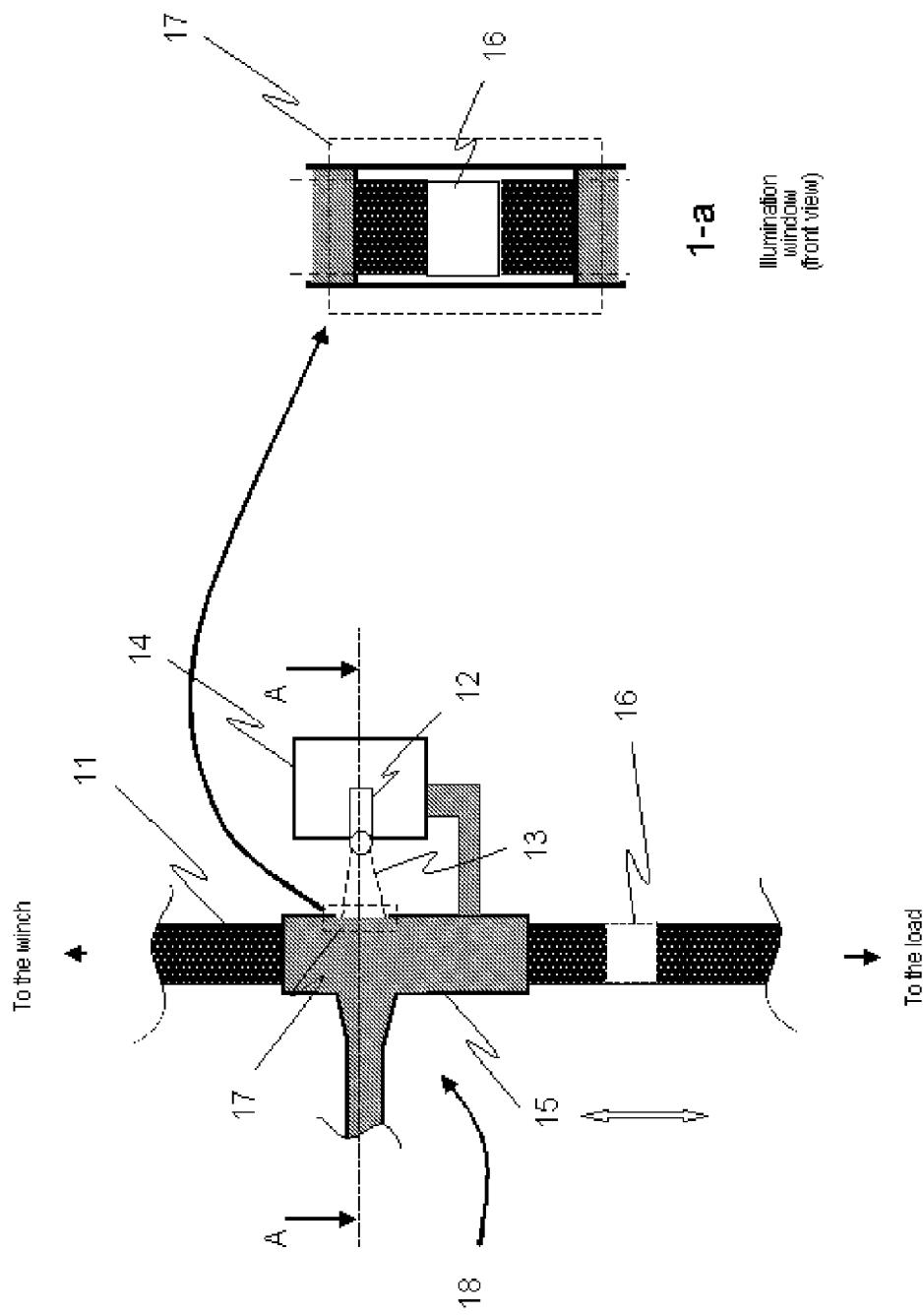
FIG. 1, a schematic illustration of an optical detection system making it possible to detect the complete winding of a cable, to which the invention can be applied.
Figure 2:
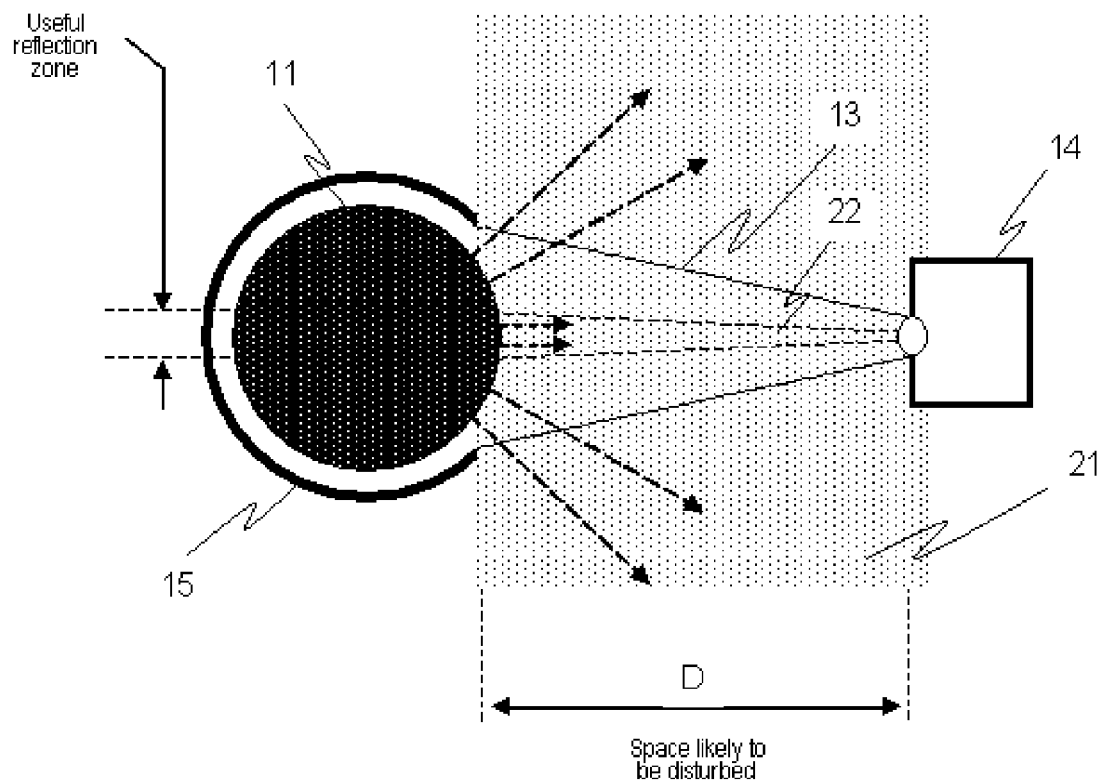
FIG. 2, a schematic representation making it possible to illustrate the problems posed by the use of an optical detection system for monitoring the state of winding of a cable on a winch.

FIGS. 1 and 2 illustrate the structure and the principle of operation of the devices known from the prior art and highlight the drawbacks of these devices.

In operation, the object attached to the winch cable is lowered to the sea from the helicopter and immersed to a given depth, while remaining attached to the winch cable, while the helicopter maintains a stationary flight vertically above the place of immersion. Then, after use, the system is raised back on board the helicopter as fast as possible so that the latter can leave its stationary position within the shortest possible delay.

During the raising operation in particular, it is useful to have a means enabling the winch operator to be informed, other than "by sight", of the fact that the object that is being raised has arrived at a planned position for which the final phase of onboard recovery of the object can be performed. The final phase consists mainly in slowly winding the cable so as to slowly raise the object on board the helicopter, either to unhook it from the cable and place it in an appropriate storage location, or to secure the movements of the object if the latter is simply placed on the platform of the winch and remains moored to the winch when it is not in use, or even to completely moor the object if the latter is maintained in a suspended position at the end of the cable.

This is why, while the raising of the object is mainly performed at high speed, the latter has to be performed much more slowly when the object approaches the platform. In this zone, the raising of the object has to be able to be stopped instantaneously so as to avoid any risk of abrupt collision with the platform supporting the winch, a collision that might damage the object or the winch, but also the helicopter itself. During this final raising phase, during which certain handling operations are sometimes necessary, the winding of the cable is generally controlled manually.

To this end, as schematically illustrated by FIG. 1, there is generally, placed under the boom of the winch, a mechanical structure 18 configured to ensure the guiding of the cable 11 in the first part of its descent, a structure on which an optical detection device 14 is mounted. The optical detection device 14, which comprises a source 12 emitting a light beam 13 and means for detecting the light beam reflected by an object illuminated by the emitted beam, is generally configured and arranged in such a way as to emit its light beam 13 in the direction of the cable 11 so as to illuminate the latter over a zone delimited by the dimensions of the beam 13. In the example of FIG. 1, the mechanical structure 18 comprises a cylindrical channel 15, which can have a lateral opening (not visible in the figure) allowing for the insertion of the cable 11, this cylindrical channel 15 being provided with an opening 17 that is sufficient to allow passage for the light beam 13 emitted by an optical detection device 14 mounted on the structure, in a position as close as possible to the cable, and oriented in such a way that the emitted light beam 14 is aimed at this opening 17. However, in the context of the invention, the structure 18 can comprise any means making it possible to guide the cable in the initial part of its travel and illuminate the cable over a delimited zone (i.e. a section).

Such a device is generally intended to detect, by the detection of a reflected power difference, a section 16 of the cable 11 whose surface is made more reflecting than that of the rest of the cable. To this end, the surface of this section 16 can, for example, be covered with a white paint, the rest of the surface of the cable being naturally steel gray.

In other words, the system comprises means for forming a colored reference mark on a section of the cable. The colored reference mark is a zone that is more reflecting than the surface of the rest of the cable. This zone is a zone of the surface of the section of the cable.

This particular section 16 is in theory situated in proximity to the free end of the cable, to which the object (i.e. the load) is hooked. Thus, during the raising of the object, the winding of the cable 11 onto the winch naturally brings the section 16 of the cable into the zone illuminated by the beam 13 from the detection device 14, so that, the reflection of the emitted beam being greater, it is possible to determine that the winding of the cable 11 is almost completed and that the final phase of recovering of the object must be undertaken, a phase for which the rewinding of the cable 11 has to be performed at reduced speed.

Such an arrangement, known from the prior art, presents the advantage of simplicity. In fact, its implementation requires only the placement of an optical detector 14 on the mechanical structure 18 that already exists and of a suitably determined reflecting marking on a section 16 of the cable 11. However, it presents certain limitations which render its operation sometimes uncertain, particularly in the case of a winch used to lower and raise an object intended to be immersed in the sea to a certain depth, an immersion which involves that of the cable.

In such circumstances, the rapid raising of the cable leads to the formation, in proximity to the cable, from its surface, of a zone of nebulosity consisting of fine droplets originating from the film of water driven by the cable in its removal from the water during its rewinding. The droplets that are thus present in the vicinity of the cable have the effect of altering the transmission of the beam 13 toward the surface of the cable and the reflection of the emitted beam, in the direction of the detector of the device 14.

The consequences of this phenomenon can therefore consist in spurious detections by reflection of the beam 13 by the droplets of water in suspension, spurious reflections which arise indiscriminately whether the illuminated zone of the cable is or is not the zone 16 made reflecting. These spurious reflections sometimes cause the winding speed of the cable 11 to be limited too early and thereby delay the departure of the helicopter from the zone concerned.

The consequences of this phenomenon can also consist of an absence of detection at the right time, the beam emitted or reflected by the zone 16 of the cable made reflecting for this purpose being diffused by the medium and consequently not returned to the detector and therefore not detected. This is reflected in a fast winding speed being maintained at the end of rewinding, which can prevent the final phase of recovery of the object from proceeding correctly and cause damage to the assembly.

The presence of this zone of nebulosities is all the more damaging to the optical detection system since the latter is generally positioned as close as possible to the cable, for reasons of optical effectiveness that are obvious to those skilled in the art. As illustrated in FIG. 2 (cross-sectional view in the horizontal plane passing through AA), this phenomenon is reflected in the presence, between the detector and the surface of the cable illuminated by the detector, of a space 21, of width D, likely to be disturbed from the point of view of the propagation of the light waves.

To resolve this problem brought about by the presence of a zone that can alter the propagation of the light waves, the detection device according to the invention has added to it means making it possible to ensure an optimal propagation of the light waves between the detection device 14 and the cable 11. According to the invention, these means consist in placing, between the detection device 14 and the cable 11, a light waveguide. This light waveguide is advantageously arranged in such a way that the light waves that are propagated between the cable and the detection device are propagated in the waveguide. In other words, the waveguide guides the light waves that are propagated between the cable and the detection device (in both directions of propagation: from the cable, to the detection device and vice versa).

Advantageously, the waveguide is configured and arranged in an optimal fashion, as described hereinbelow in the text which presents several embodiments of the device according to the invention.

Figure 3:
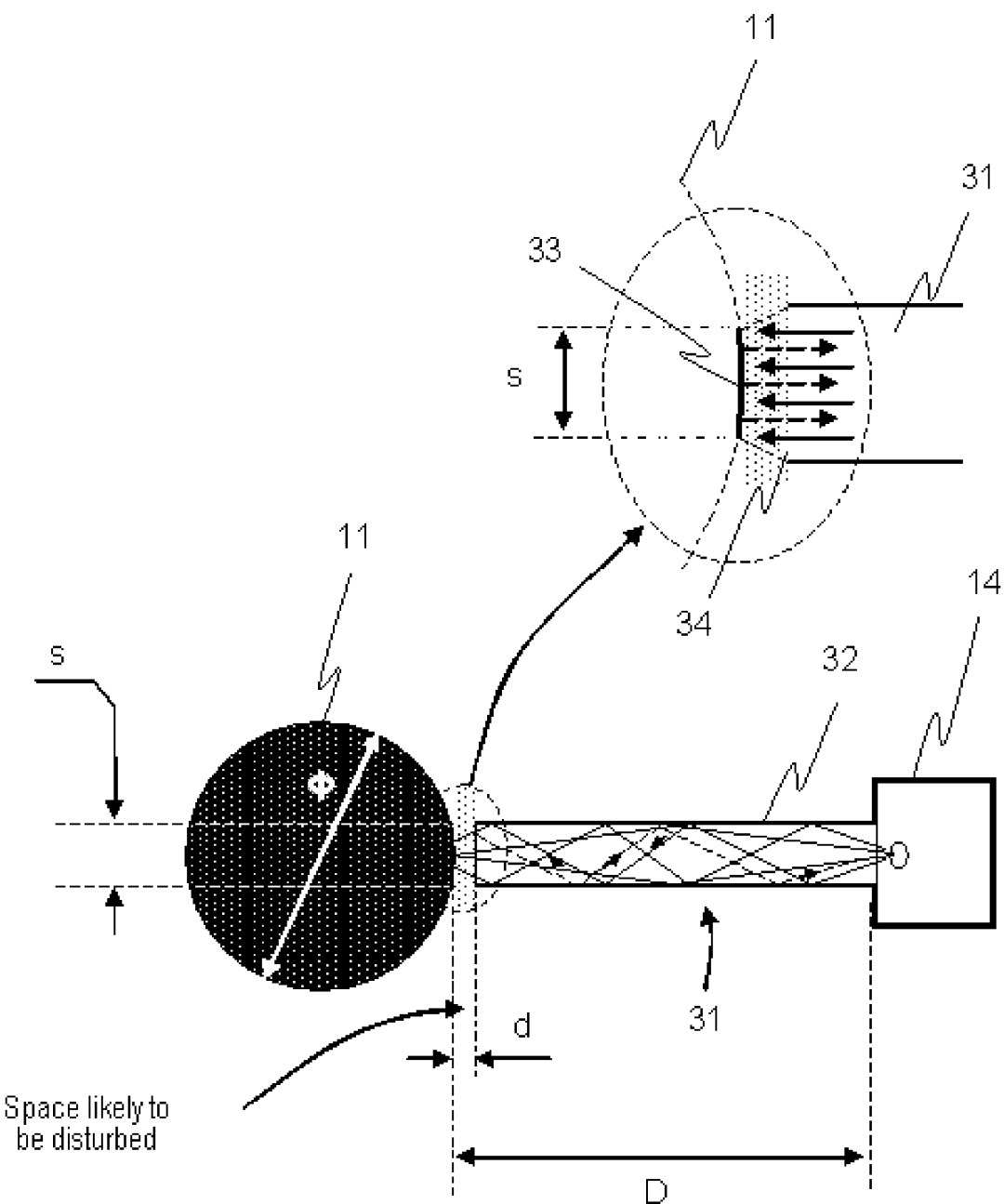
FIG. 3, a schematic illustration of the structure of the system according to the invention in a simple embodiment.

FIG. 3 shows a schematic diagram of the device according to the invention, in its simplest configuration (cross-sectional view in the horizontal plane passing through AA). The latter comprises, as described previously, an optical detector 14 comprising a source 12 emitting a light beam 13 and means for detecting the signal reflected in the direction of the source by an illuminated object, the section of the cable 11 illuminated by the beam 13 in the example considered. This device is here advantageously complemented by a light waveguide 31, arranged in such a way as to be illuminated by the source 12, the length L of which is such that the free distance separating the device from the wall of the cable is reduced to a value d substantially less than the distance D separating the actual source 12 from the cable. Thus, the space in which the propagation of the light waves between the detection device and the cable risks being disturbed by the presence of the droplets of water produced by the rapid raising of the cable is advantageously reduced.

Advantageously, the light waveguide is arranged in such a way that the detection device 14 illuminates the cable with a guided light beam 13, aimed substantially at the axis of symmetry of the cable. The dimensions of the light waveguide 31 are, furthermore, determined as a function of the section of the cable 11. In practice, as illustrated by FIGS. 2 and 3, when the light beam 13 produced by the source 12 illuminates the cable, only the portion of the beam having illuminated the surface of the cable within a narrow zone around the aimed direction is likely, because of the curvature of the surface of the cable, to be reflected in the direction of the guide 31 and therefore be received by the detector 14. The waves illuminating the surface of the cable 11 with a lower incidence are reflected in directions which do not allow them to be captured by the detection device 14. They are therefore useless from this point of view.

The diameter $\phi$ of the cable 11 thus defines the size s of the useful zone 33 of its surface, likely to reflect the beam 13 emitted by the source 12. According to the invention, the dimensions of the light waveguide are defined in such a way as to illuminate a zone totally covering the useful zone 33. As illustrated by FIG. 3, the beam 13 emitted by the source 12 is thus advantageously focused on this surface. Conversely, the light waves reflected by the latter are channeled toward the detection means of the device 14.

In a simple embodiment, such as that illustrated by FIG. 3, the light waveguide is of simple parallelepipedal form, its end faces forming rectangular planar surfaces at right angles to the main axis of the guide 31. One of its end faces 34 is positioned facing the convex surface of the cable 11. This configuration, although advantageous in terms of production, can however be optimized from different points of view.

Figure 4:
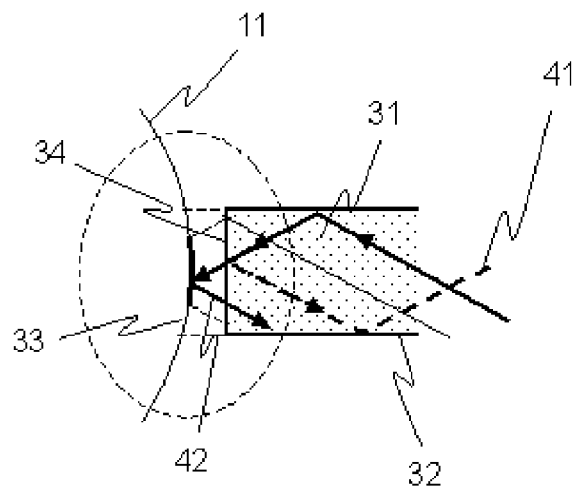
FIG. 4, an illustration highlighting an operating characteristic of the embodiment of FIG. 3.

It can in particular be optimized in such a way as to limit the spurious reflections of the beam produced by the source 12 against the wall forming the face 34 of the guide, a wall through which the light waves emitted by the source 12 are transmitted. Such reflections occur when a light wave passes through the planar surface of a crystal, regardless, moreover, of the relative orientation of the wave in relation to this surface. These spurious reflections 41, illustrated by FIG. 4, form, as is known, a background noise which has the effect of reducing the detection sensitivity of the device, the light waves 41 reflected by the face 34 of the guide 31 having, in some cases, an intensity at least comparable to that of the waves 42 reflected by the useful surface 33 of the cable 11.

Figure 5:
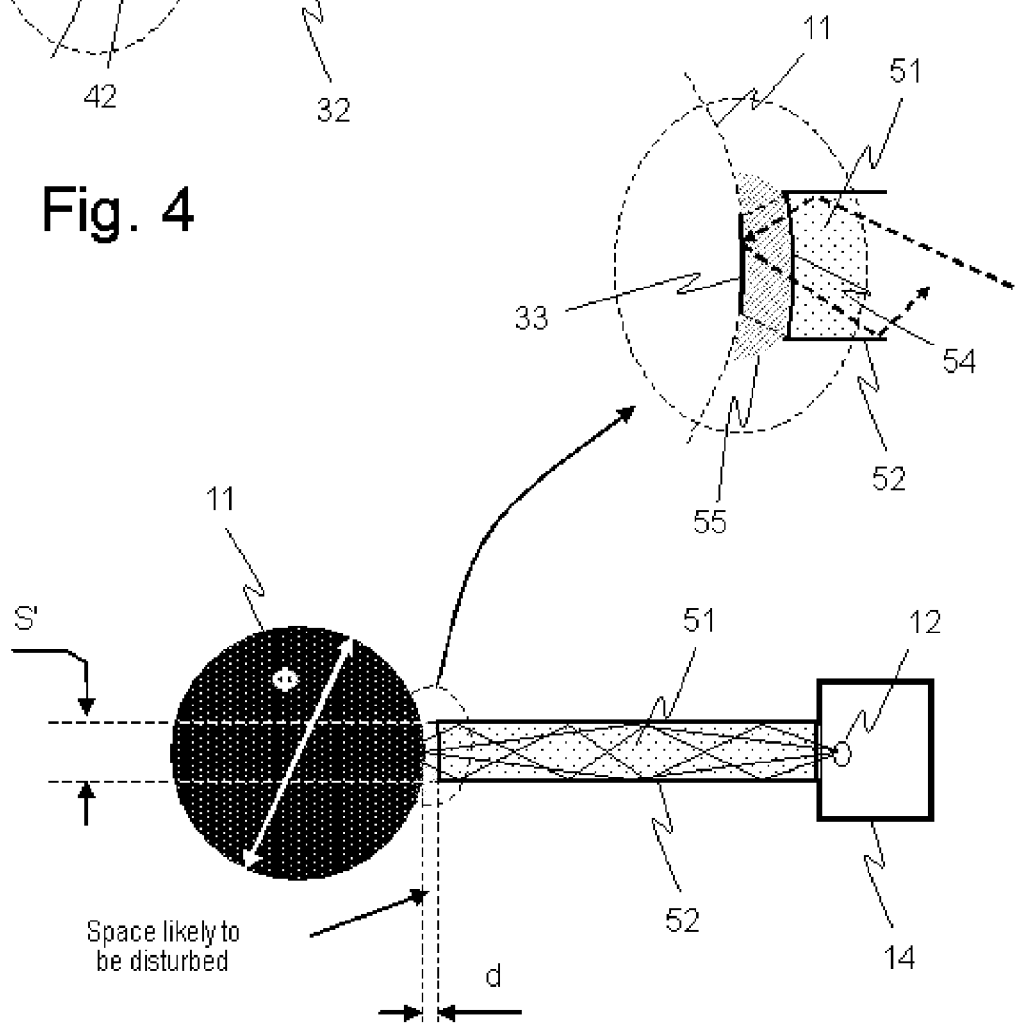
FIG. 5, the illustration of a preferred embodiment of the system according to the invention.

In order to limit these spurious reflections 41 inside the guide 31, in a preferred embodiment, illustrated by FIG. 5, a guide 51 is used in which the end face 54 has a non-planar surface, preferably a concave surface with a radius of curvature that corresponds to the diameter $\phi$ of the cable 11. This type of configuration naturally offers the advantage of limiting, to a great extent, the spurious reflections inside the guide 51 of the light beam 13 emitted by the source 12.

It should be noted that other configurations of the end face 54 can be envisaged for limiting these spurious reflections. In particular, it is possible to give this space a convex profile. The invention is not therefore limited to just the single embodiment in which the end face 54 of the light waveguide has a concave surface. Nevertheless, this embodiment offers other advantages and should be considered as a preferred embodiment:

it makes it possible, because of the concave nature of the face 54, to increase, to only a certain extent however, the dimensions of the useful zone 33 of the surface of the cable for which the reflection of the emitted beam occurs in the zone covered by the end face 54 of the guide 51.

it makes it possible, moreover, if the distance d is sufficiently small, to establish and maintain, throughout the raising of the cable 11, the presence of a film of water 55 which is positioned in the space separating the concave end 54 of the guide 51 and the surface of the cable 11. This film of water 55 advantageously establishes a continuity between the surface of the cable 11 and the waveguide 51, a continuity which favors the correct illumination of the surface of the cable 11 by the light beam 13 emitted by the source 12 and an optimal capture, without the risk of disturbances, of the light waves reflected by the useful surface 33 of the cable.

It should be noted also that, whatever the embodiment envisaged, it is possible to reinforce the effectiveness of the guiding of the light beam 13 emitted by the source 12 and of the light waves reflected by the surface of the cable 11, by applying to the lateral faces 32 (52) of the guide 31 (51), a layer of reflecting material, preferably thin, so as to minimize the losses in the guide.

Advantageously, the waveguide has a fixed end securely attached to the source 12. Advantageously, as can be seen in FIG. 5, this end is contiguous with the device 14. Advantageously, as can be seen in this figure, this end is arranged in such a way that all the waves emitted by the source and outgoing from the device 14 are propagated in the waveguide.

The invention claimed is:

1. A system for monitoring the travel of a cable wound on a winch, the system comprising:
    an active optical detection device placed upstream of a winding zone of the cable at a given distance from the winding zone;
    a means for forming a colored reference mark on the cable, the colored reference mark providing a section of a surface of the cable that is more reflective than a rest of the surface of the cable; and
    a light waveguide interposed between the active optical detection device and the cable, wherein the light waveguide has a free end directed toward the cable, and the free end of the light waveguide has a concave surface concentric with the surface of the cable,
    wherein the active optical detection device includes:
    a light source emitting a light beam toward the cable, and
    means for receiving light waves reflected by the surface of the cable illuminated by the light beam, and
    wherein the light waveguide guides the light beam and the light waves reflected by the surface of the cable,
    wherein the light beam is configured to illuminate a zone of the cable situated in a zone of illumination,
    wherein the cable is configured to move relative to the zone of illumination and water is driven according to a movement of the cable,
    wherein a length of the light waveguide is defined such that the water driven by the cable forms a film of water between the free end of the light waveguide and the surface of the cable, and
    wherein the film of water fills a space between the free end of the light waveguide and the surface of the cable and enhances a guiding of the light waves reflected by the surface of the cable toward the active optical detection device.

2. The system as claimed in claim 1, wherein the light waveguide has a fixed end securely attached to the light source.

3. The system as claimed in claim 1, wherein a length of the light waveguide is defined such that a distance between the free end of the light waveguide and the cable is minimized.

4. The system as claimed in claim 1, wherein the light waveguide has lateral faces covered with a layer of reflecting material.

5. The system as claimed in claim 1, wherein the light waveguide has a length such that a free distance separating the active optical detection device from the surface of the cable is substantially less than a distance separating the light source from the cable.

* * * * *